(12) United States Patent
Rodenburg

(10) Patent No.: US 9,116,120 B2
(45) Date of Patent: Aug. 25, 2015

(54) THREE DIMENSIONAL IMAGING

(75) Inventor: John Marius Rodenburg, Sheffield (GB)

(73) Assignee: Phase Focus Limited, Sheffield (GB)

( * ) Notice: Subject to any disclaimer, the term of this patent is extended or adjusted under 35 U.S.C. 154(b) by 1264 days.

(21) Appl. No.: 12/601,219

(22) PCT Filed: Feb. 25, 2008

(86) PCT No.: PCT/GB2008/000620
§ 371 (c)(1),
(2), (4) Date: Jun. 7, 2010

(87) PCT Pub. No.: WO2008/142360
PCT Pub. Date: Nov. 27, 2008

(65) Prior Publication Data
US 2010/0241396 A1    Sep. 23, 2010

(30) Foreign Application Priority Data
May 22, 2007 (GB) ................................. 0709796.7

(51) Int. Cl.
*G01N 21/47* (2006.01)
*A61B 6/00* (2006.01)
(Continued)

(52) U.S. Cl.
CPC ............ *G01N 21/4795* (2013.01); *A61B 6/483* (2013.01); *A61B 6/5205* (2013.01); *A61B 8/00* (2013.01); *G01N 21/4788* (2013.01); *G01N 21/49* (2013.01); *G01N 23/04* (2013.01); (Continued)

(58) Field of Classification Search
CPC .................. H04N 13/0022; H04N 2013/0081; H04N 13/011; G06T 15/00; G06T 7/0065

USPC ............. 345/419; 378/4–20, 70–90; 382/154; 356/603; 850/1–18; 250/307, 310
See application file for complete search history.

(56) References Cited

U.S. PATENT DOCUMENTS 5,432,349 A * 7/1995 Wood et al. ................. 250/336.1
6,771,418 B2 * 8/2004 Oh et al. ........................ 359/368
(Continued)

FOREIGN PATENT DOCUMENTS

WO WO2005/004188 A    1/2005
WO WO2005/106531 A    11/2005

OTHER PUBLICATIONS

Rodenburg, J. M., et al. "Hard-x-ray lensless imaging of extended objects." Physical review letters 98.3 (2007): 34801.*
(Continued)

*Primary Examiner* — Ke Xiao
*Assistant Examiner* — Whitney Pointe
(74) *Attorney, Agent, or Firm* — Wilmer Cutler Pickering Hale and Dorr LLP

(57) ABSTRACT

A method and apparatus are disclosed for providing image data for constructing an image of a region of a three dimensional target object. The method includes the steps of providing incident radiation, via at least one detector detecting an intensity of radiation scattered by the target object, repositioning incident radiation relative to the target object, subsequently detecting the intensity of radiation scattered by the target object, determining a probe function indicating an estimate of at least one characteristic of the incident radiation at one or more depths of the object and providing image data from which an image of one or more regions of the object may be constructed via an iterative process using the probe function.

45 Claims, 11 Drawing Sheets

(51) Int. Cl.
| | |
|---|---|
| *A61B 8/00* | (2006.01) |
| *G01N 23/225* | (2006.01) |
| *G01N 23/04* | (2006.01) |
| *G06T 11/00* | (2006.01) |
| *G01N 21/49* | (2006.01) |

(52) U.S. Cl.
CPC .......... *G01N23/046* (2013.01); *G01N 23/2251* (2013.01); *G06T 11/003* (2013.01); *A61B 6/466* (2013.01)

(56) References Cited

U.S. PATENT DOCUMENTS 6,826,424 B1 * 11/2004 Zeng et al. .................... 600/476
8,836,695 B2 * 9/2014 Park et al. .................... 345/419

OTHER PUBLICATIONS

Rodenburg, J. M., A. C. Hurst, and A. G. Cullis. "Transmission microscopy without lenses for objects of unlimited size." Ultramicroscopy 107.2 (2007): 227-231.*

Rodenburg, J. M., et al. "Hard-x-ray lensless imaging of extended objects." Physical review letters 98.3 (2007): 034801.*
International Preliminary Report on Patentability and Written Opinion of the International Searching Authority, mailed Dec. 3, 2009, for corresponding International Application No. PCT/GB2008/000620.
International Search Report and Written Opinion of the international Searching Authority, mailed Jul. 25, 2008, for corresponding International Application No. PCT/GB2008/000620.
Chapman, Henry N., "Phase-Retrieval X-Ray Microscopy by Wigner-Distribution Deconvolution: Signal Processing," *Scanning Microscopy*, vol. 11: 67-80, 1997.
Nugent, Keith A., "X-Ray Noninterferometric Phase Imaging: A Unified Picture," *J. Opt. Soc. Am A*, 24(2):536-547, Feb. 2007.
Plamann, et al., "Electron Ptychography. II. Theory of Three-Dimensional Propagation Effects," *Acta Cryst.*, A54:61-73, 1998.
Rodenburg, et al., "Transmission Microscopy Without Lenses for Objects of Unlimited Size," *Ultramicroscopy*, 107:227-231, 2007.
Rodenburg, et al., "Hard X-Ray Lensless Imaging of Extended Objects," *Physical Review Letters*, 98:034801, Jan. 19, 2007.
Spence, et al., "Phase Recovery and Lensless Imaging by Iterative Methods in Optical, X-Ray and Electron Diffraction," *Phil. Trans. R. Soc. Lond. A*, 360:875-895, 2002.

* cited by examiner

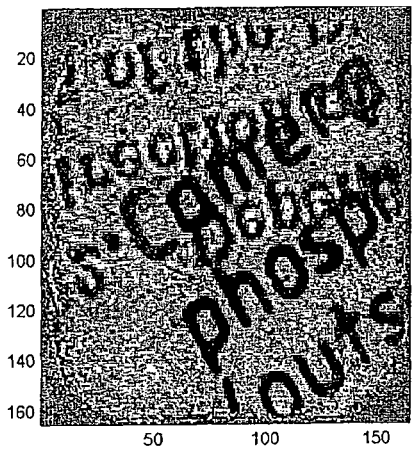
11a
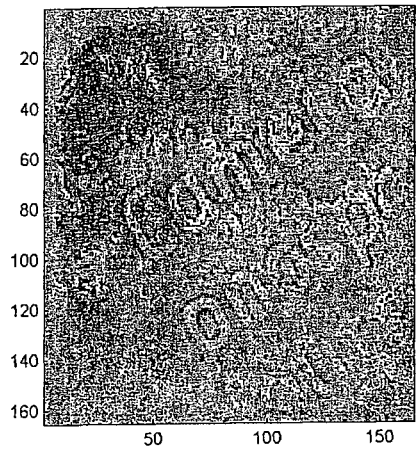
11b
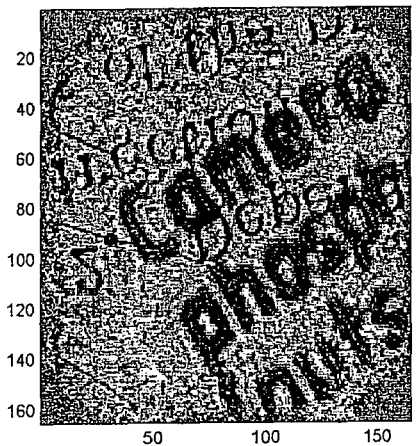
11c
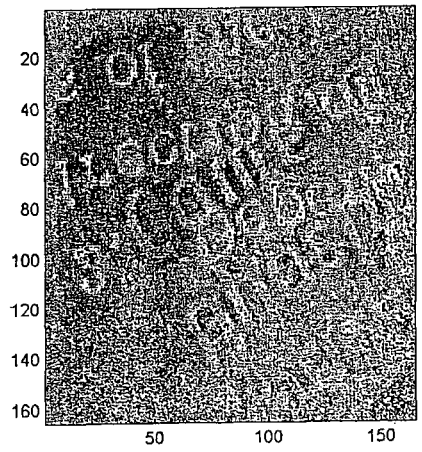
11d
FIG 11

THREE DIMENSIONAL IMAGING

CROSS REFERENCE TO RELATED APPLICATIONS

This is the U.S. National Stage of International Application No. PCT/GB2008/000620, filed Feb. 25, 2008, which in turn claims the benefit of Great Britain Application No. GB0709796.7, filed May 22, 2007.

The present invention relates to a method and apparatus for providing image data from which an image of a target object may be generated. In particular, but not exclusively, the present invention relates to a method and apparatus for obtaining a through-focal series from a data set. When combined the series can be used to examine the three-dimensional (3D) structure of a target object.

Many types of imaging techniques are known for deriving spatial information about a target object (otherwise referred to as a specimen). For example, and as shown in FIG. 1, in conventional transmission imaging, an object is irradiated by plane wave illumination 10. The waves scattered by the object are re-interfered by a lens 12 to form an image. In the case of very short wavelength imaging (X-rays or electrons) this technique has many known difficulties associated with aberrations and instabilities introduced by the lens which limit the resolution and interpretability of the resulting image. Typical achievable resolution is many times larger than the theoretical wavelength limit.

Conventional scanning transmission imaging is another example of an imaging technique in which a lens is used to focus a spot of radiation through a target object. One or more detectors are located on the post target side (i.e. downstream) of a target object to detect scattered radiation. Various types of detector strategies are known such as annular detectors, quadrant detectors and/or off-axis detectors. However these methods rely on scanning the focused spot of radiation to all points where an image of the target object is required. There are a number of problems associated with such techniques such as the fact that very accurate control of the spot is required because if a 1000×1000 pixel image is desired a million accurate probe-position points must be used. Another problem is that the lens used must be of a very high quality. Not only is this because the resolution of the final image is only as good as the sharpness and localisation of the spot but also because with various forms of radiation such as electrons or X-rays there are many problems such as aberration effects, chromatic spread and lens current instability which can affect image production and can ruin resolution. This is shown schematically in FIG. 2 in which incident radiation 15 such as an electron or X-ray beam is incident upon a specimen 16 forming the target object. Radiation scattered by the object exits the target object and propagates onto detector plane 17.

Known problems with conventional scanning transmission imaging are that the images take a large time to complete due to the number of points which must be probed with the incident spot of radiation. Also if the target object moves during data collection this can lead to inaccurate data being collected and ultimately inaccurate images being produced. Still further conventional scanning transmission imaging methods do not allow information relating to the phase of the radiation exiting the target object to be measured. Only total scattering intensity at the detectors can be measured. As such phase information relating to the exit wave that emanated beyond the target object cannot be gathered.

A modification of conventional scanning transmission imaging is four-dimensional de-convolution imaging. This technique utilises similar apparatus to that shown in FIG. 1 but records a whole diffraction pattern for every probe position. This provides a way of determining the structure of the target object at a better resolution than the spot size or response function of the lens used but has a number of major problems. The most notable problem is that huge quantities of data must be recorded which take hours to collect for a reasonable field of view. This makes the experiment practically very difficult to carry out because it is essential to control the probing illumination very accurately and to move it accurately to scan every (million) pixel for the final image reconstruction. Also severe damage or destruction can occur to the target object because huge doses of incident radiation are required for the large times taken.

Another well known imaging technique is pure diffractive imaging. In this alternative strategy the lens may be omitted and a target object is illuminated by a simple plane wave of probing radiation. The scattering pattern measured in the far field forms a Fourier plane diffraction pattern and the intensity of this may be recorded. An iterative method is then used by applying information derived from the intensity measured to calculate an estimated object exit wave field. In order to determine real information about the target object from the estimated wave field an area in real space must be provided where it is known that the object is absent or masked in some defined way. Only by knowing this fact can a running estimate of the wave field representing the object can be iteratively altered. There are however a multitude of problems associated with pure diffractive imaging. Most notably the target object must be suspended or isolated at some fixed location in some way. This is practically very difficult to achieve. Also it is not possible to extend the solution to new or different parts of the object or get a large image all at good resolution. Only one isolated region of an object can be illuminated and solved for. Also the target object must be single valued. That is, it must be represented by a single real number. That number may represent an absorption or a phase change but may not represent both. In fact most real target object waves (that is the wave function associated with illumination exiting a target object) appear as complex numbers having both phase and amplitude components.

Another major problem with pure diffractive imaging is that the edge of the target object must be sharply defined and thus have a distinct edge. This is so that an area where it is known that the object is absent or masked in some way is well defined. In practice it is difficult to produce an object or aperture having such a defined edge.

Further problems are that for weakly-scattering objects, which is a common type of target object in X-ray and electron scattering, most of the radiation passing through the object ends up at the centre of the diffraction pattern. Information in this zone is wasted as it does not aid in the image forming process but the radiation passing through the object can damage the object. Also parallel illumination is required. However this means that for a source of given brightness relatively few counts are provided at the object plane. In combination with the fact that much radiation passing through weakly-scattering objects terminates in a central zone as noted above this means that the whole experiment in practice takes a long time to get enough counts. If during the data collection stage the object or some other imaging apparatus drifts or moves during exposure data may be ruined.

Many of the above-mentioned imaging techniques permit only two dimensional analysis of a target object. From time to time it is helpful to be able to examine the three-dimensional (3D) structure of a target object. This is true in a broad range of transmission imaging techniques, such as those mentioned above, using any type of wave illumination, such as photons, electrons, neutrons, atoms, etc, all of which behave as a wave once they have momentum. In examining 3D structure of a 3D target object, a through-focal series needs to be obtained. Such a through-focal series when stacked together as a 3D data set can then be used to examine the 3D structure either in real time or at some later date. A user can choose particular features of interest or locations within the structure which are to be examined.

Such a through focal series can be obtained, by way of example, in a conventional microscope (light, electron, X-ray etc) by using a lens. As the focus control of the lens is varied the images seem to pick out one layer in the specimen at a time. Volumes of the object which are above or below the selected plane of interest (the plane on which the lens is focused) appear in such an image as an out of focus background image. According to prior known techniques, the focusing of the lens can be carried out in a number of ways. For example, in the case of light or X-rays the objective lens can physically be shifted (or indeed the whole microscope shifted) towards or away from the sample. Alternatively, the sample may be moved towards or away from the lens whilst keeping the lens focused on the same plane in space. In the case of electrons which use electromagnetic (electrostatic or magnetic) lenses the power, voltage and/or current or other such parameter in or on the lens can be varied thus effecting a change in the strength of the lens. In this way focusing on layers above or below a current plane of interest can be controlled. Again, as an alternative, the target object specimen may be moved physically with respect to the lensing device.

However, with such known techniques, the image so-obtained is measured in intensity alone. This means that phase changes induced in the waves as they travel through the object are not observable. There are a number of known technologies for using a through focal series to solve for the phase of the waves but all of these require a complex, accurate and well controlled lensing scheme.

There are a number of further problems associated with known techniques for acquiring 3D information about 3D objects. A first major problem as noted above is that known techniques require a lens. In the case of imaging techniques using light, the lens inherently gets in the way of the sample restricting access particularly at very high resolution imaging steps. In the case of many other types of radiation used as a source of illumination to probe the target objects, such as electrons, X-rays, ultraviolet and terahertz frequencies, good quality lenses are not available. All lenses are expensive.

Another problem associated with prior art known techniques for 3D examination of a 3D target object is that a series of images must be collected. Each image in the series of images requires a different defocus (achieved as above described) thus exposing an object to a considerable dose of radiation and potentially taking a considerable amount of time. Radiation is a serious problem for imaging many classes of target objects which may sustain irrevocable damage under X-ray or electron radiation. In such objects it is not possible to form rapidly-exposed images.

It is an aim of embodiments of the present invention to at least partly mitigate the above-mentioned problems.

It is a further aim of embodiments of the present invention to provide a method and apparatus for providing image data which may be used to construct a high resolution image of a 3D target object as well as high resolution images of selected areas or layers in the object.

It is an aim of embodiments of the present invention to provide a method and apparatus which enable the 3D structure of a target object to be examined without the need for high resolution positioning techniques to position incident radiation relative to a target object.

It is an aim of embodiments of the present invention to provide a method and apparatus for examining a 3D target object using a wide variety of probing illumination without destroying or substantially damaging the target.

According to a first aspect of the present invention there is provided a method of providing image data for constructing an image of a region of a three dimensional (3D) target object, comprising the steps of:

providing incident radiation, from a radiation source, at a 3D target object;

via at least one detector, detecting the intensity of radiation scattered by said target object with the incident radiation at a first position with respect to the target object;

re-positioning the incident radiation relative to the target object;

subsequently detecting the intensity of radiation scattered by said target object with the incident radiation at a second position with respect to the target object; and determining a probe function, indicating an estimate of at least one characteristic of the incident radiation, at one or more depths in the 3D object; and providing image data, from which an image of one or more regions of the object may be constructed via an iterative process using said probe function.

According to a second aspect of the present invention there is provided apparatus for providing image data for generating an image of at least one region of a target object, comprising:

a radiation source for providing incident radiation at a 3D target object;

at least one detector device for detecting an intensity of radiation scattered by said target object;

a locating device that selectively locates the target object at two or more pre-determined locations with respect to the incident radiation; and a processor that provides the image data responsive to a detected intensity of the scattered radiation at two or more locations; wherein the said processor is arranged to provide image data indicating structure of regions at respective depths within said 3D target object.

Embodiments of the present invention use an iterative method to provide image data which may be used to examine the 3D structure of a 3D target object. The methodology used can be carried out without the requirement for a lens capable of high precision focusing. Rather, only a localised field of illumination, which may be large relative to the wavelength of the particular radiation field used, is needed. This may be provided by a poor lens, able for example to produce an imperfect or approximate focusing effect, or by an aperture which permits radiation from a source to form a localised illumination function.

Embodiments of the present invention provide a method and apparatus in which the detector and optics used for making an illumination function can be distant from a target object. As such good access to the specimen is maintained at all times.

Embodiments of the present invention provide a method and apparatus in which a target object is only exposed to radiation once or perhaps a few times rather than many times or for a prolonged period of time. This prevents destruction of or damage to the target object.

Embodiments of present invention permit 3D examination to take place "off-line". In other words at any time subsequent to the collection of data which is used during the examination process. This enables the structure of the 3D target object to be examined by focusing into various parts of the target object at some later date as desired. It is to be noted that alternatively the examination can occur in "real-time".

Embodiments of the present invention will now be described hereinafter, by way of example only, with reference to the accompanying drawings in which:

FIG. 11 illustrates intensity and phase results for a simple three-dimensional object consisting of two separated planar objects.

In the drawings like reference numerals refer to like parts.

Figure 1:
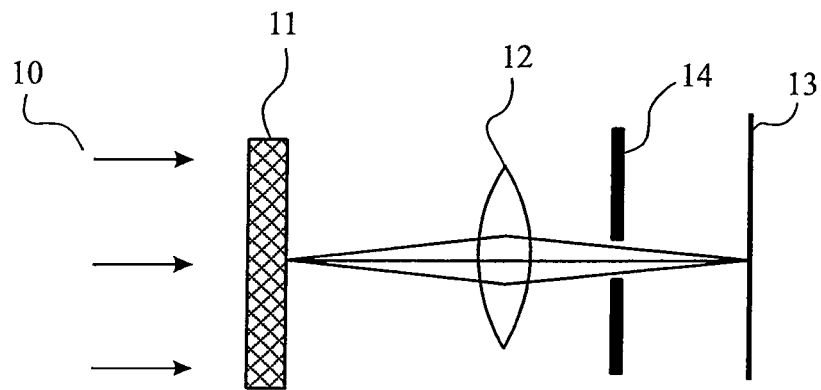
FIGS. 1 and 2 illustrate use of conventional transmission imaging and conventional scanning transmission imaging respectively.
Figure 3:
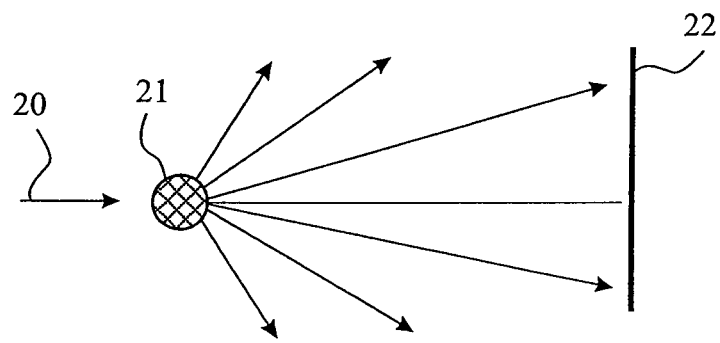
FIG. 3 illustrates how diffraction does not limit angular range.
Figure 2:
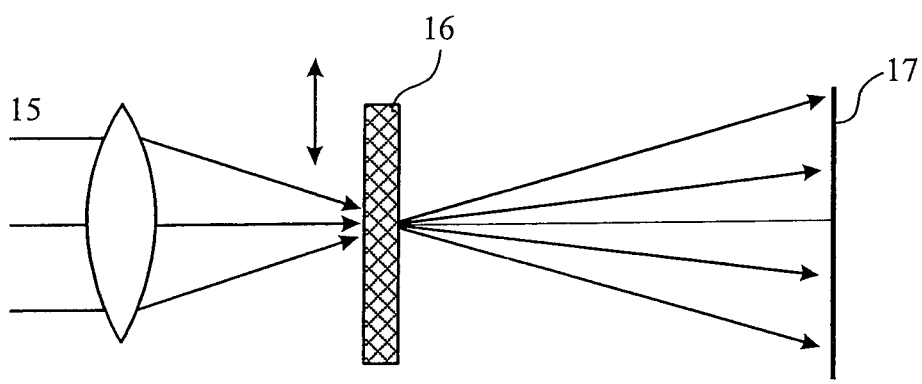
Figure 4:
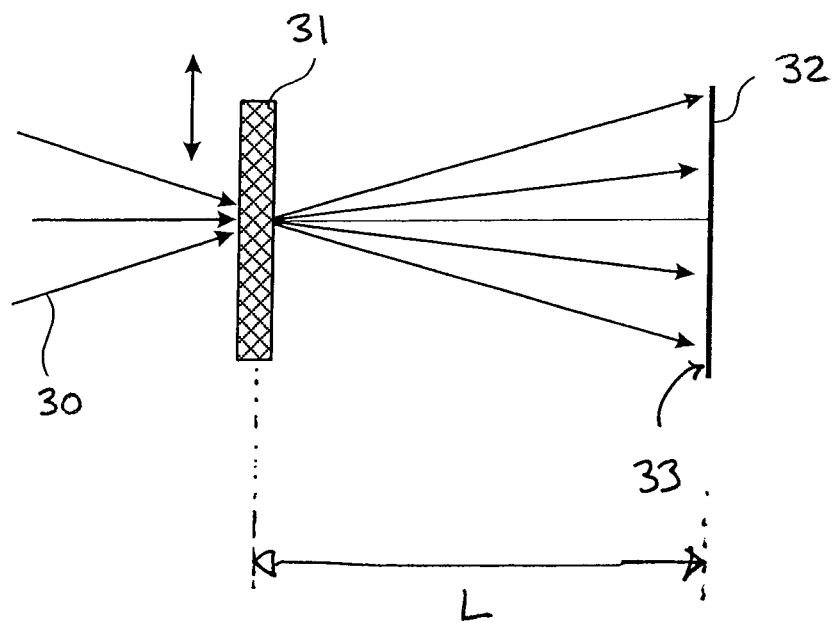
FIG. 4 illustrates how a moving focused probe allows a large field of view to be measured.

FIG. 4 illustrates how a scattering pattern may be developed and used to determine high resolution information about the structure of a three dimensional (3D) target object. It will be understood that the term target object refers to any specimen or item placed in the path of incident radiation which causes scattering of that radiation. It will be understood that the target object should be at least partially transparent to incident radiation. The target object may or may not have some repetitive structure.

Incident radiation 30 is caused to fall upon the target object 31. The radiation illuminates the target object. In this sense it will be understood that illumination does not necessarily imply use of radiation having a wavelength in the visible spectrum. Rather it is to be understood that the term radiation is to be broadly construed as energy from a radiation source. This will include electro magnetic radiation including X-rays, emitted particles such as electrons and/or acoustic waves. Such radiation may be represented by a wave function $\psi(r)$, where r is a three-dimension vector describing a position in space. This wave function includes a real part and an imaginary part as will be understood by those skilled in the art. This may be represented by the wave functions modulus and phase. $\psi(r)^*$ is the complex conjugate of $\psi(r)$ and $\psi(r) \cdot \psi(r)^* = |\psi(r)|^2$ where $|\psi(r)|^2$ is an intensity which may be measured for the wave function.

The incident radiation 30 is scattered as it passes through and beyond the specimen 31. As such the wave disturbance within the illumination volume is altered in amplitude and phase by the object and so alters the amplitude and phase of the wave downstream of the object function. Thus characteristics of the incident radiation are modified as a result of propagating through and after the specimen. If an array of detectors such as a CCD detector 32 is arranged a long distance from the specimen then a diffraction pattern is formed at a diffraction plane 33. A Fourier diffraction pattern will form if the detectors 32 are located a distance L from a selected part of the specimen where L is sufficiently long for the diffraction pattern to be formed effectively from a point source (a substantially small illumination volume at the object plane). If the diffraction plane is formed closer to the specimen, by locating the detectors nearer, then a Fresnel diffraction pattern will be formed. A device, such as a lens or nearby aperture, is used to confine the illumination within a small region of the object. Prior art techniques require the object to be finite or illuminated by a sharply defined illumination function, so that certain regions in the object plane are known not to give rise to any scattered waves. Mathematically this is described as the object wave having a support, wherein the scattering outside the support region is zero. In contrast, the region illuminated for use with embodiments of the present invention need not be strongly localised and sharply defined. They may be slowly varying at their edges. In this way the softly varying illumination function is not necessarily composed of high spatial frequencies. In other words it can be a bandwidth limited function that may formally be infinite in extent, although substantially localised.

Embodiments of the present invention take intensity measurements at a distance from the 3D target object and use this data in an iterative process described below to generate data which can be used to make an estimate of the 3D structure of the object. To collect the data an illumination function of some type is made incident upon the object of interest. The illumination can be generated by a broad range of situations, for example the illumination may be generated by a lens of some sort or an aperture upstream of the object or any other sort of optical arrangement which can generate a beam-like illumination which is substantially located within a volume of the object say of diameter D. Intensity data can then be collected downstream of the object perhaps in the Fourier domain or Fresnel diffraction pattern region as noted above. A broad range of detector arrangements can be utilised since all that needs to be known about the detector is the general configuration so that a calculation can be carried out of a propagation function of a wave in a selected object plane to the detector. Variations involved may include geometric variations in the way that spherical wavelets are added together according to Huygen's principle. For example, a flat detector could be mounted downstream of the object at some angle with respect to the direction of the incident radiation, and at a point relatively near the object (in the Fresnel diffraction condition). Those skilled in the art will understand that in order to calculate the intensity or phase of the wave over the surface of such a detector, an integral can be performed (that is say, an alternative integral transform is defined, referred to as $T^{+1}$ below, over the volume of the specimen). Each elemental volume of the object will scatter a spherical wave which will have a particular intensity and phase as it impinges upon the detector. At large angles of scatter, the amplitude of this wave may be modified by an obliquity factor or scattering function, as well-documented in the prior art. This intensity and phase, as well as depending on the object's scattering characteristics, will also be affected by path length between the elemental volume of the object and a point on the detector. The exact path length could be calculated using trigonometry, accounting for the particular arrangement of the elemental volume of the object relative to the point on the detector. The path length may also determine a change in the total amplitude of the wave, as the spherical wave amplitude decays with propagation. In general, an integral transform could therefore be constructed accounting for the angled detector or, indeed, any configuration of detector. In this context, the Fresnel and Fourier integrals are examples of such integral transforms corresponding to geometrically simple approximations. Such integral transforms will be denoted T in what follows. The particular embodiment we describe will assume that this transform is the Fourier transform, it being understood that any suitable integral transform relating to other detector configurations can be substituted for the Fourier integral.

Figure 5:
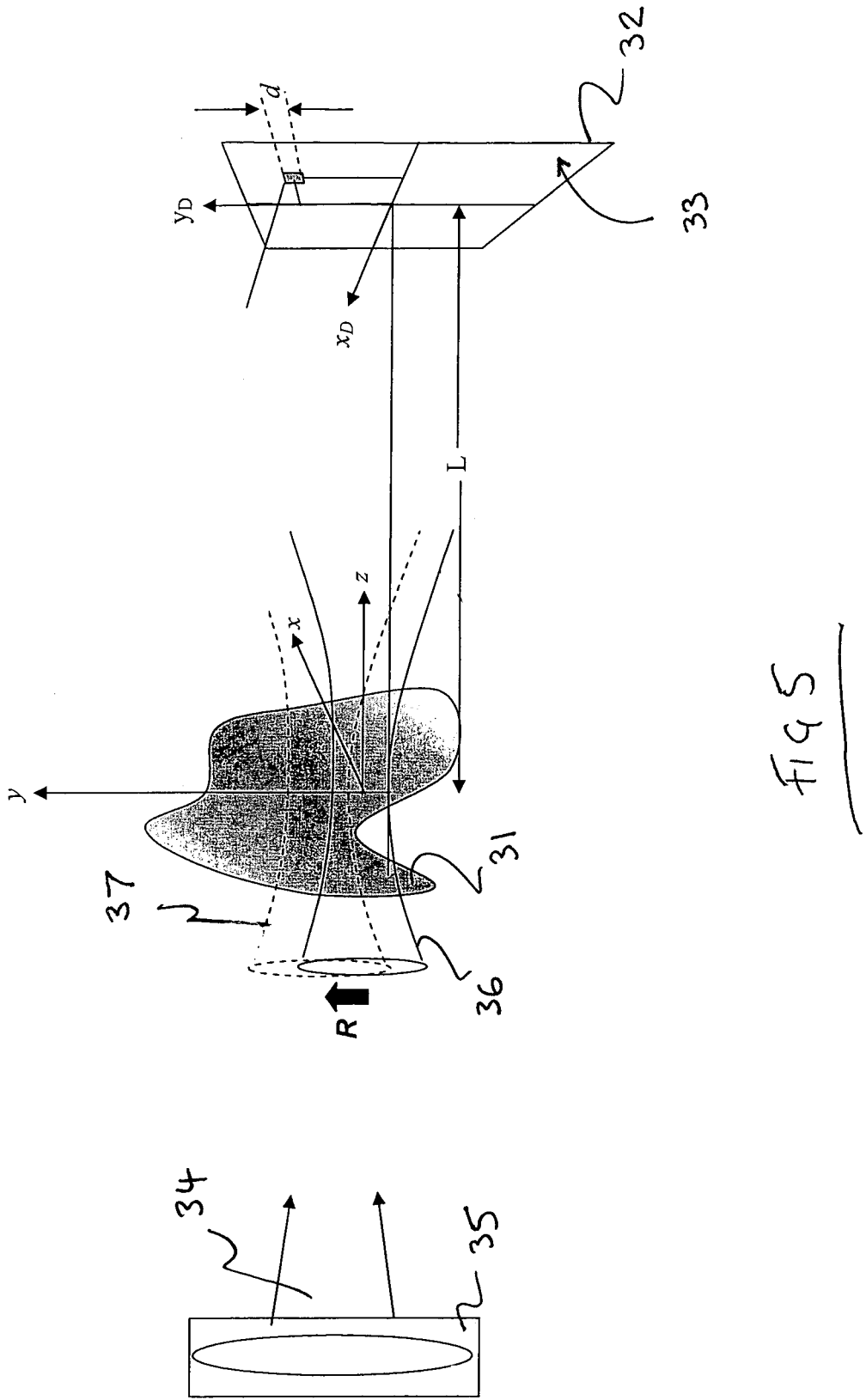
FIG. 5 illustrates a 3D target object and detector plane.

FIG. 5 illustrates an example of this process in more detail. The radiation 34 is roughly focused, for example by a weak lens or aperture, labelled 35, so that a first volume of the target object is illuminated by the wave profile labelled 36. The radiation can be moved to another position, 37, displaced from the first position by the vector R. The weak lens may of course comprise any appropriate focusing apparatus such as a set of plates and a voltage supply for a beam of electrons or a reflective surface or zone plate for X-rays. The weak focusing is sufficient to substantially confine the probing radiation beam. It is thus not necessary to sharply focus radiation although of course strongly focussed radiation could be used. Further positions can be utilised if desired.

With respect to this FIG. 5 Cartesian coordinates x,y,z, can be defined where z lies in a direction towards the detector. It will be understood that the exact direction relative to the detector is not fundamental. Let the object, which is three-dimensional, be denoted by O(r), where r is a vector as described above, but which can alternatively be decomposed into Cartesian components x,y and z. It is assumed that each elemental volume of O(r) can introduce phase changes or modulus attenuation in any illuminating wave that passes through it. Embodiments of the present invention relate to a method of obtaining an estimate of the structure of O(r) in three dimensions. It is assumed that O(r) has an extent and size such that part of it is substantially confined to the z-coordinate around z=0, although it may be entirely upstream (but near) z=0, or downstream (but near) z=0, or, preferably, having its depth in z embracing z=0. There are no limits on the size of O(r) in the x-y directions.

The illuminating radiation incident on the target object consists of a probe function P(r) which forms an illumination function in three-dimensional space, wherein r is also a three-dimensional vector, such as that generated by a caustic or illumination profile formed by the lens or other optical component. P(r) is the complex stationary value of this wave field calculated throughout a volume of space in which the object of interest is located. It may be moved by a distance represented by the three-dimensional vector R, so that for a particular value of R, the probe is represented by P(r−R). The wave function ψ(r,R) defines the phase and modulus of radiation scattered by the object for each point in r, and for a particular position, R, of the illumination. Once the scattered and transmitted wavelets from each volume of the object have traversed space to the detector, they will add in amplitude and phase, and thus generate an intensity distribution (e.g. a Fresnel or Fraunhofer diffraction pattern) I(u,v,R), where u and v are coordinates defining a position in the detector plane, for the particular illumination position R.

The detector shown in FIG. 5 has a flat surface positioned downstream of the object, say at a distance L. For the simplicity of the exposition in this embodiment, the detector lies in a plane parallel to the z-axis, i.e. in the plane (x,y,L), and L has been chosen to be large so that the detector lies in the Fourier (Fraunhofer) diffraction plane. The physical width and height of square pixels in the detector are designated as of size d, and $x_D$ and $y_D$ describe the coordinates of any one such pixel in the detector plane. According to the small angle approximation of the tangent function, we can say that, approximately;

$$\Delta\beta = \frac{d}{L} \quad (1)$$

where Δβ is the solid angle in either the x- or y-directions subtended by the (square) side of the detector pixel at the object plane. We now define the coordinates;

$$u = \frac{\sin\beta_x}{\lambda} \quad (2a)$$

$$v = \frac{\sin\beta_y}{\lambda}. \quad (2b)$$

where $\beta_x$ and $\beta_y$ are given by:

$$\beta_x = \tan^{-1}\left(\frac{x_D}{L}\right) \quad (3a)$$

and $$\beta_y = \tan^{-1}\left(\frac{y_D}{L}\right) \quad (3b)$$

In the operation, intensity measurements are made at various pixels in the detector and, for a particular position of the illumination function, R, these are then arranged into an array I(u,v,R) in a computer or other processing unit or data store according the transformations described above.

In what follows, a convention is adopted that a plane wave can be described by the equation;

$$\psi(r)=Ae^{i2\pi k \cdot r} \quad (4)$$

where r is a three-dimensional vector as defined above and k is a reciprocal space vector that points in a direction perpendicular to planes of constant phase in the plane wave. A is complex number whose modulus and phase describe the modulus and phase of the wave at the point x=y=z=0. The magnitude of k is given by;

$$|k| = \frac{1}{\lambda} \quad (5)$$

where λ is the wavelength of the radiation used. Note that only the spatial dependence of the wave is considered, that is, solutions of the time-independent wave equation. It is also assumed that the radiation is substantially monochromatic so that all the k-vectors of interest will have the same magnitude. It is nevertheless true that the method of imaging described here will work for illumination that consists of a small range of k-vector magnitudes (i.e. is only 'substantially' coherent).

$$T_{x,y}^{+1}f(x,y)=\iint f(x,y)e^{i2\pi(ux+vy)}dxdy=F(u,v) \quad (6a)$$

defines the forward Fourier transform of a two-dimensional function f(x,y) which maps onto the coordinates u and v (equations 2), and $$T_{u,v}^{-1}F(u,v)=\iint F(u,v)e^{-i2\pi(ux+vy)}dxdy=f(x,y) \quad (6b)$$

defines the corresponding back Fourier transform. Of course, for a detector configuration not lying so far from the object, as described in this particular embodiment, a Fresnel or other propagation integral may be more appropriate as will be appreciated by those skilled in the art.

Figure 12:
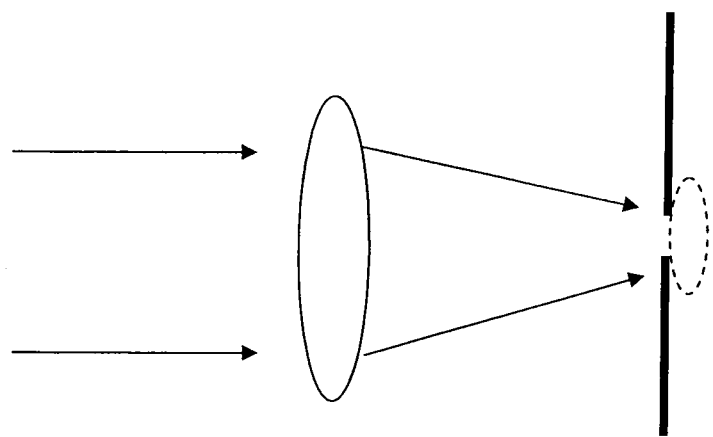
FIG. 12 illustrates an alternative radiation source configuration.

The illumination function which is incident upon the object can be estimated over a plane in the space near the object. In the case of the illumination being generated by a lens or optical component, the (known) aberrations in the lens can be used to calculate the illumination function in such a plane. If an optical component such as a (known) aperture lies in such a plane, then it can be assumed that the wave is of constant phase over the plane of the aperture, the amplitude being determined by the shape of the aperture. Alternatively, a known object function can be used to solve for the illumination function in a way analogous to the method described below, but with the mathematical representations of the object and illumination function exchanged. In some embodiments where available illumination intensity is low, it may be advantageous to use a lens to condense intensity upon an aperture or other optical component, as shown in FIG. 12, the phase and amplitude at the final optical component upstream of the object being calculated by a combination of the methods above.

Figure 6:
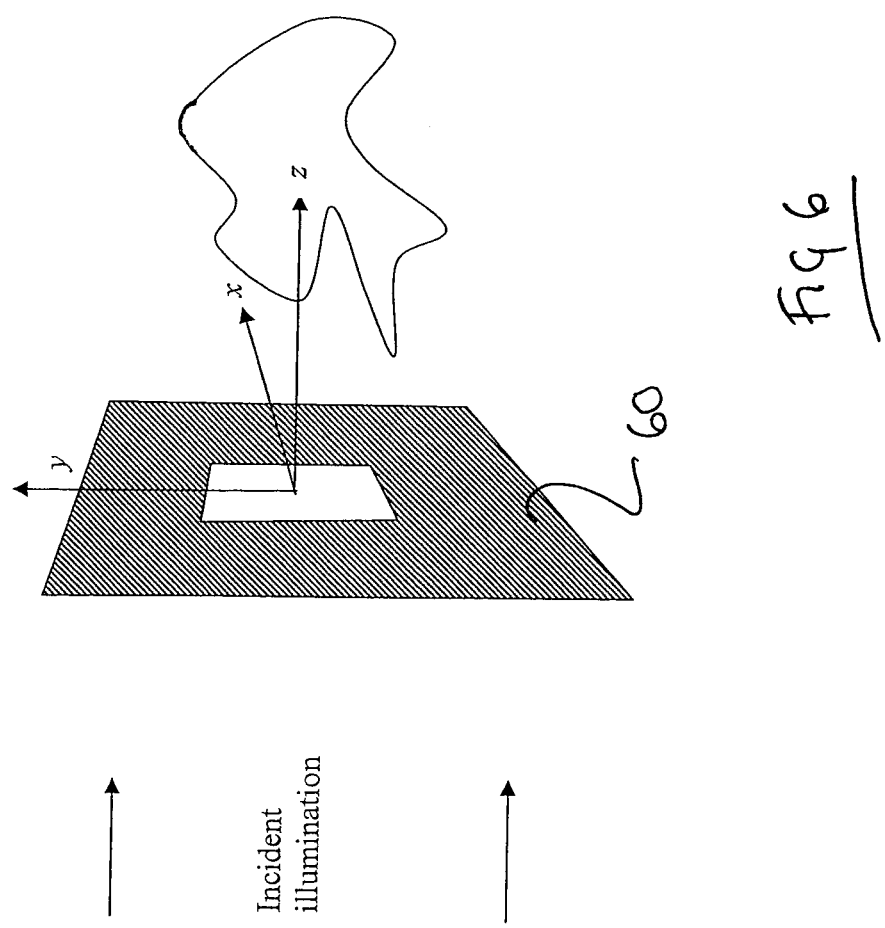
FIG. 6 illustrates a pre-target aperture.

For example, we may know that an aperture 60 exists close to the object in the plane lying in x and y where z=0. This is illustrated in FIG. 6. Since the time evolution of the wave is not considered to play a part (because illumination is considered temporally coherent), the wave-field immediately downstream of the aperture can be described by a function, P(x,y, 0), it being understood that this represents the complex value (describing the modulus and phase) of the illumination function in the plane z=0. In everything that follows, it is advantageous that P(x,y,0) is substantially localised in the sense that it only has large modulus at values of |x| and |y| less than D, where;

$$D = \frac{\lambda}{\Delta \beta} \quad (7)$$

where $\Delta\beta$ is the angle subtended by the width (or height) of a detector pixel at the point x=y=z=0. In the case of the small angle scattering approximation, D can also be expressed as above in terms of the "camera" length L and the physical width (or height) of the detector pixel, as;

$$D = \frac{\lambda L}{x_D} \quad (8)$$

P(x,y,0) can be expressed in terms of a Fourier sum of a set of plane waves incident upon the plane z=0. These plane waves comprise an angular spectrum, each incident plane wave k-vector being described also by the angular coordinates u and v, as depicted in FIG. 5. Such an angular spectrum can be represented by A(u,v), it being understood that this can be represented as a 2-dimensional array pixels, each of which has a complex value which determines the modulus and phase of the particular plane wave lying at the angular coordinate u and v.

Figure 7A:
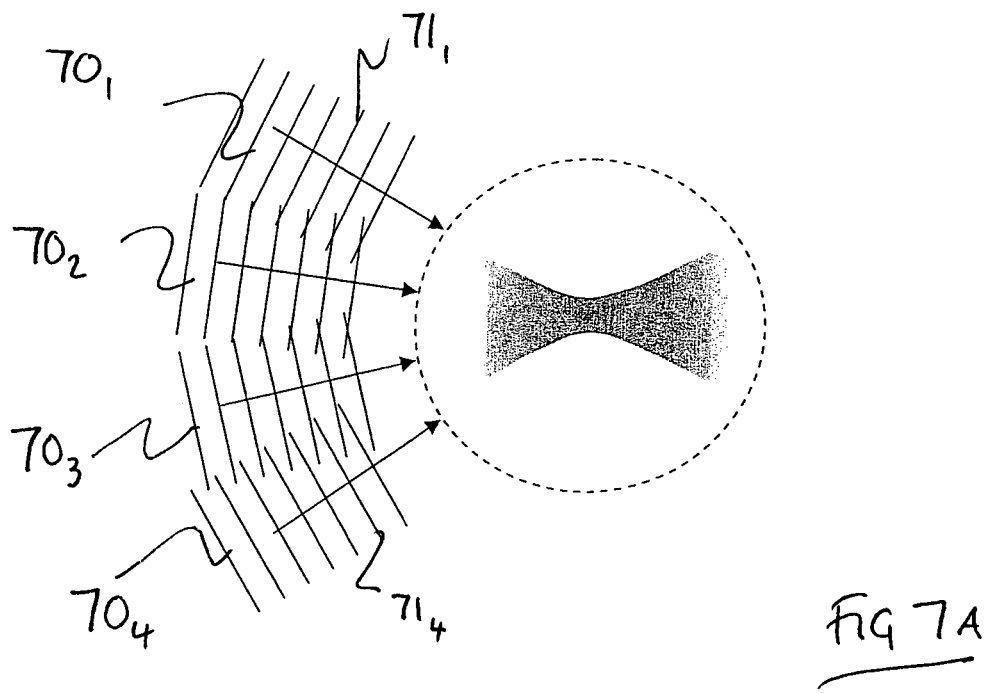
FIGS. 7A and 7B illustrate k-vectors of incident plane waves.
Figure 7B:
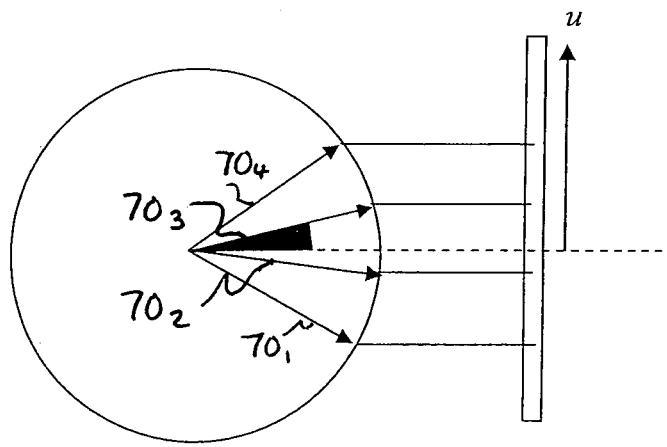

FIGS. 7A and 7B illustrate the relationship between the incident k-vectors and the coordinates u, v, as represented in a computer array or some other such processing unit or data store. 70₁, 70₂, 70₃ and 70₄ show k-vectors of incident plane waves which form a 3D illumination function (within the dotted sphere). All the k-vector are of the same length, but are incident at different angles. The parallel lines 71₁-71₄ show the planes of constant phase for each of these incident waves. In FIG. 7B the vectors are rearranged, so that they all subtend from a common origin. A cross-section through the 2D array is shown representing this distribution of k-vectors (and hence the corresponding real-space representation of the 3D illumination function P(x,y,z)). Each value of this array (shown as a function of u, with v=0) has a complex value associated with it, which describes the amplitude and phase of the plane wave component lying at the angle $\beta_x$, as defined in equation 2a. In this diagram, $\beta_y$=0. $\beta_x$ for the k-component is shown labelled 70₃.

Such an angular spectrum can be generated conveniently by a weakly focused lens wherein the function A(u,v) can be thought of lying over a spherical surface emanating from the exit pupil of the lens. In the case of a lens with an aperture lying in its back focal plane, A(u,v) is of the form of a circular disc of radius w, where all values $w > (u^2+v_2)^{1/2}$ have zero modulus. Values of A(u,v) lying within this disc can have phases determined by aberrations in the lens, or moduli dependant on the evenness of the illumination of the lens.

The relationship between P(x,y,0) and A(u,v) is given via the Fourier transform;

$$P(x,y,0) = \iint A(u,v) e^{i2\pi(ux+vy)} du dv = T_{x,y}^{+1} A(u,v) \quad (9)$$

It being understood that the two-dimensional Fourier transform over A(u,v) produces the illumination function in the x-y plane with z=0.

If only P(x,y,0) is known (say an aperture is located in the plane z=0) then the corresponding distribution A(u,v) required to generate this function can be calculated via the Fourier transform $$A(u,v) = \iint P(x,y,0) e^{-i2\pi(ux+vy)} dx dy \quad (10)$$

An estimate of P(x,y,z) can be calculated as follows. This is the illumination function that fills a region of three-dimensional space in the vicinity of the object. Form:

$$P(x,y,z) = T_{u,v}^{-1}(A(u,v) \cdot e^{i\phi(u,v,z)}) \quad (11)$$

where $$\phi(u, v, z) = \frac{2\pi z}{\lambda}\left(1 - \cos\left(\sin^{-1}\left(\lambda(u^2 + v^2)^{\frac{1}{2}}\right)\right)\right). \quad (12)$$

Similarly generate P(x,y,z) from only having a knowledge of P(x,y,0) via the step:

$$P(x,y,z) = T_{u,v}^{-1}((T_{x,y}^{+1} P(x,y,0)) \cdot e^{i\phi(u,v,z)}). \quad (13)$$

In the equations above the convention of labelling the Fourier operators by subscripts defining the coordinates over which they operate has been adopted. In other words, to form P(x,y,z) for a particular plane in z, we Fourier transform P(x,y,0) with respect to the x and y coordinates and multiply by a phase function, $e^{i\phi(u,v,z)}$, for the particular value of z of interest, and then Fourier transform back.

If only very small angles of scattering are considered (as in the case of electron wave propagation), then $$\phi(u,v) \approx \pi \lambda z (u^2 + v^2). \quad (14)$$

P(x,y,z), which henceforth we will be written using the vector notation r as P(r), is incident upon an object function O(r), and it is possible to move the P(r) with respect to the x or y coordinates by distances X, Y, Z. In other words, in vector notation, P(r−R) can be formed. Therefore the illuminating function can be shifted to give P(r−R), or the object function shifted to give O(r−R). In what follows, only the situation of moving the illumination function is discussed, it being understood that according to embodiments of the present invention either or both of the object or the illumination can be moved and that in many actual implementations it may be move convenient to move the object rather than the illumination.

The disturbance in the wavefield caused by the object function (whether it lies upstream, downstream or at the plane of z=0) is therefore given by:

$$\psi(r)=P(r-R)\cdot O(r) \quad (15)$$

A data set I(u,v,R) is measured in the far field over the coordinates u and v (as specified by the angular transforms in equations 2a and 2b for two or more values of R, where these values of R, say $R_1$ and $R_2$, are preferably chosen such that the illumination moves to a position which partly overlaps with a volume of the object which has also been illuminated by at least one other illumination function when positioned at some other value of R. It should be understood that to obtain a wide field of view of the object, the number of R positions may be large, the preferred procedure being that for any one $R_n$ illumination position there is at least one other illumination position $R_m$ which substantially overlaps with the volume irradiated at the illumination position for R.

Figure 8:
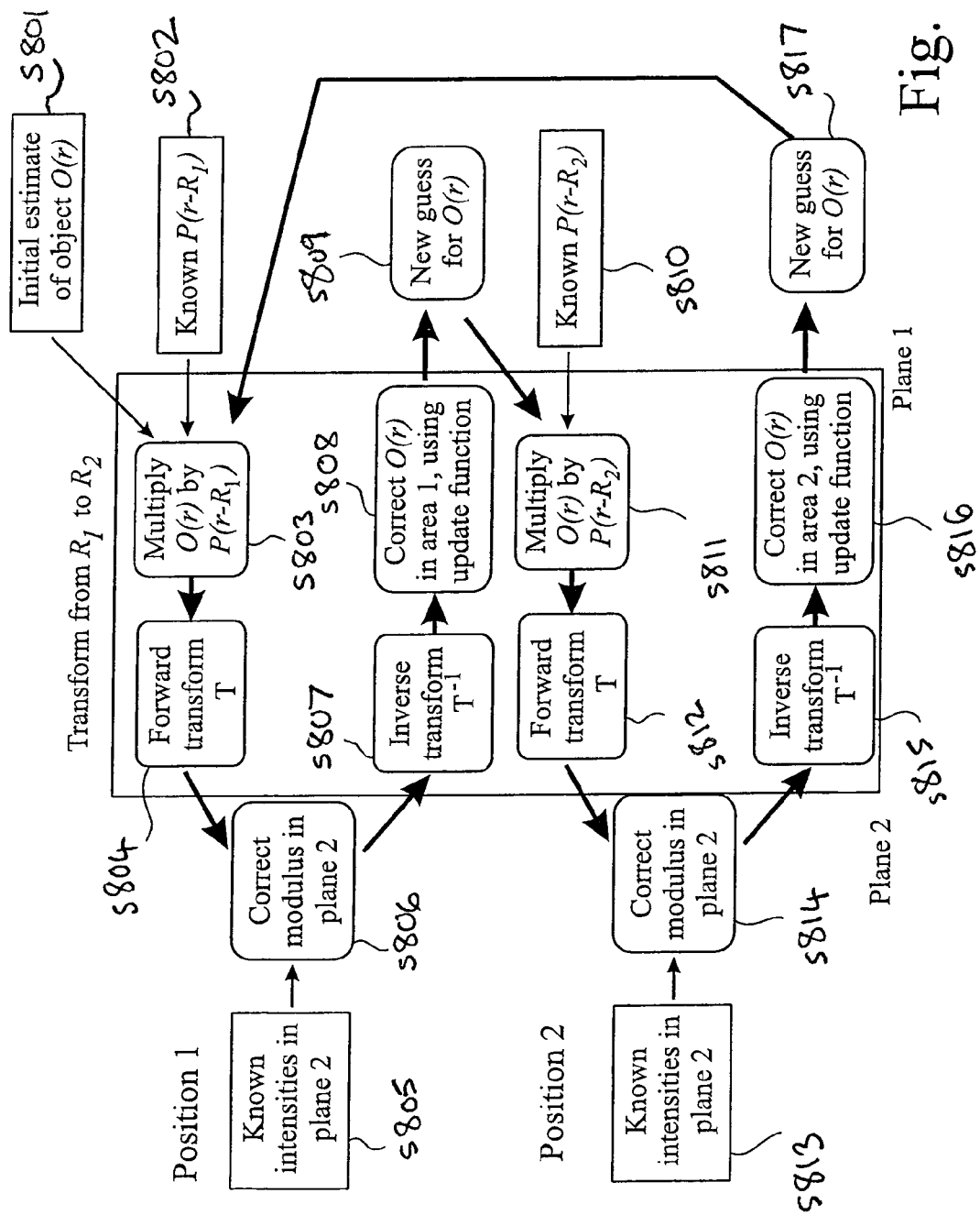
FIG. 8 illustrates an iterative process.

Data is processed according to the iterative process illustrated in FIG. 8. Preferably the process starts by assuming an empty object function s801, so that O(x,y,z)=O(r) has a value of unity over all its coordinates. As the processing proceeds, the value of O(r) is continuously updated. The $n^{th}$ estimate of O(r) is labelled $O_n(r)$.

At step s802 a known probe function at the location in the target object which is to be examined and which has previously been measured or estimated is provided.

It will be appreciated that as noted above the probe function may be determined in a number of different ways depending upon the convenience required. For example the probe function can be determined if a known aperture located at a predetermined distance from the target is utilised. Alternatively an optical arrangement with calculated or known values may be used or still further a probe function can be determined earlier by placing a known object in the path and reverse calculating what the probe function must be to produce measured intensity results. In any event once the probe function is known the next step is:

$$\psi_g(r,R)=P(r-R)\cdot O(r)=\psi_g(x,y,z) \quad (16)$$

is formed as per equation 15.

This provides an estimate of the scattered wave function at the plane of interest in the target object. In order to provide an estimate of this wavefield at the detector plane 33 a forward transfer of the guessed wave function is made at step s804 by forming $M_g(u,v,z)$ according to the following equation:

$$M_g(u,v,z)=T_{x,y}^{+1}[\psi_g(x,y,z)] \quad (17)$$

it being understood that this Fourier transform is only taken with respect to the x and y coordinates, so that each slice over z=constant in $\psi_g(r)$ is Fourier transformed over its x- and y-coordinates and placed into the slice in $M_g(u,v,z)$ at z=constant. $M_g(u,v,z)$ is now broken down into its modulus and phase components, such that:

$$M_g(u,v,z)=|M_g(u,v,z)|e^{i\Theta_g(u,v,z)} \quad (18)$$

For the particular illumination function position being processed, R, a diffraction pattern, I(u,v,R) is stored. This is the known intensity in plane 2 at position 1 shown in FIG. 8 and provided at step s805. Next the square root of this intensity is formed and at step s806 the modulus of $M_g(u,v,z)$ shown in equation (18) is replaced with the square root of this intensity, such that:

$$M_c(u,v,z)=\sqrt{I(u,v,R)}e^{i\Theta(u,v,z)} \quad (19)$$

Note here that the same modulus (measured only over the coordinates in u and v) is applied to the pixels lying at any one value of z in $M_c(u, v, z)$. However, the phase which is applied, $\Theta(u,v,z)$, will in general be different at different values of z.

Next $M_c(u,v,z)$ generated with equation 19 is inverse transformed at step s807 according to:

$$\psi_c(x,y,z)=T_{u,v}^{-1}[M_c(u,v,z)], \quad (20)$$

This provides a corrected estimate of the wave function in real space, the back Fourier transform being undertaken only over the u and v coordinates.

A next estimate of the object function $O_{n+1}(x,y,z)=O_{n+1}(r)$ is constructed at step s808 by putting:

$$O_{n+1}(r)=O_n(r)+U(r)(\psi_{c,n}(r)-\psi_{g,n}(r)), \quad (21)$$

Here U(r) is given by:

$$U(r)=\frac{\beta|P(r-R)|^l P^*(r-R)}{|P_{max}(r-R)|^l(|P(r-R)|^2+\delta)} \quad (22)$$

where the parameters β, δ and l are appropriately chosen, and $|P_{max}(r-R)|$ is the maximum value of the amplitude of P(r-R). The result is a new guess for the object function (s809).

The update function helps make the effective deconvolution that occurs possible and introduces a weighting factor which causes the object function to be updated most strongly where the probe function has largest amplitude. The selectable constant l may be set to 1. It may be selected as any value in the range of 0 to 3 and need not be an integer value. It is useful to set l>1 when there is much noise. l may be selected l<1 when because of scattering geometry, the detected intensity is of the form of a Gabor hologram or similar. The value δ is used to prevent a divide-by-zero occurring if |P(r-R)|=0. δ is a small real number as is commonly applied in Weiner Filters and is usually (though not necessarily) smaller than $P_{max}$ and can be considerably smaller if the noise present in the recorded data is small. The constant β controls the amount of feedback in the algorithm, and may advantageously be varied between roughly 0.1 and 1. When β=less than 0.5, the previous estimate of the object is considered to be more important than the new estimate. Values in between vary the relative importance of the two estimates. β determines how quickly a solution is reached.

δ is a parameter which may be set at a fixed value or which may vary. It indicates how noisy the recorded data is and is used to attenuate how the updating is carried out in response to these circumstances. If good conditions exist for data collection that is to say with high beam current (high flux), which would imply low shot-noise, then it is safer to use results gathered to update the guessed estimate. Consequently the value of δ can be a small fraction of $P_{max}$ (e.g. less than $\frac{1}{10}^{th}$).

The expression:

$$\frac{|P(r-R)|^l}{|P_{max}(r-R)|^l} \quad (23)$$

maximises the update effect of regions where |P(r-R)| is large. This is useful, since it is those regions which are receiving the highest amount of incident radiation, and therefore which contain information with a relatively high signal to noise ratio. This information is clearly more valuable than that from regions where very little radiation is incident, and which is heavily affected by noise.

For the situation where β=1, l=0 and δ=0, and the function P(r-R) is a mask that is can be represented by a region where its value is unity while it is zero elsewhere, or support function, the algorithm has some similarities to the well known Fienup algorithm. If in this situation, only one position R is used, then the algorithm reduces to being mathematically identical to the basic Fienup algorithm. Where more than one position R is used, the algorithm has considerable advantages over known methods, including the fact that it does not suffer from uniqueness issues, and that a wider field of view may be imaged.

Subsequent to updating the running estimate of the guess the process shown in FIG. 8 progresses to selecting data collected from a new position R which preferably at least in part overlaps the previous position. The overlap should preferably be more than 20% and is preferably 50% or more. The collection of the data may be achieved by either moving an aperture by a predetermined amount or by causing the illuminating radiation shown in FIG. 5 to fall upon a different region of the target. It will be understood that embodiments of the present invention may successfully provide image data for one location of a target object without any change in location of an aperture or incident radiation being made. In such embodiments after step S808 the algorithm returns to step S802. Instead of the initial estimate of the object function O(r) being loaded in the new guess for O(r) of step S808 is loaded in at step S809. On each iteration the new guess for the object function will approximate closer and closer to the actual object function as on each iteration information of the known intensity and thus the known amplitude component of the incident radiation is added to improve the accuracy of the estimate.

Nevertheless the more preferable method is next to process data collected from a new position of R which preferably in part overlaps the previous position as shown in FIG. 8.

A known probe function $P(r-R_2)$ at the second position is identified at step S810 and then the step as above mentioned are repeated so that the new guess generated in step S809 is multiplied with the new known probe function identified at step S810. This is illustrated in step S811. Effectively this generates a new estimate of the wave scattered by the illumination function throughout the volume of the object. The resulting scattered wave function is propagated at step S812 to provide an estimate of the scattering pattern which should be detected at that position. The diffraction pattern data measured with the illumination at position $R_2$ is provided at step S813 which gives intensity information and thus amplitude information about the transformed wave function. The intensity information is used to correct the amplitude of the transformed wave function whilst phase information is retained at step S814. This corrected wave function is inversely propagated via Fourier transformation (when the image is formed in the far field), Fresnel transformation (when the image is formed at a location where Fresnel diffraction dominates) or by any other suitable transformation. This is illustrated at step S815. The running estimate of O(r) is then corrected according to the update function shown above at step S816 and the result is a new guess for the object function illustrated in step S817.

At this stage, the data collected at the first illumination position can be used for further iteration of the processing algorithm. Alternatively, further movement of the illumination or aperture may be made to a third or further position, and a third set of data collected. Again a location where some overlap occurs between previous illuminated locations is preferable. In this way the whole target object may optionally be mapped. Alternatively the new guess generated at step S817 may be repeated without further positioning using the known diffraction pattern results. It will be appreciated that embodiments of the present invention can be used when only one position of illumination with respect to the target object is provided. In FIG. 8 the iterative method is illustrated as being repeated by returning to step S803 in which the new guess generated at step S817 is input to the multiplication stage rather than the initial estimate of the object function supplied at step S801.

It should be understood that the iterative loop illustrated in FIG. 8 can be performed many times using the same data collected from the various illumination positions, R, and that the number of R is itself unlimited. The entire iterative procedure may be undertaken at a later date using previously collected data. Furthermore, if only specific layers or cross-sections of the object are of interested, only those values of z need be processed at any one time, although, once the data is collected the user can choose to refine the value or values of z which are of interest and can repeat the iterative calculation to reveal any or all planes through z.

The iterative method may be repeated until a predetermined event occurs. For example the iteration may be repeated a predetermined number of times, for example 1000 times or until the sum squared error (SSE) measured in the difference between the experimental intensity data collected at the detector (for one or many probe positions) and the estimated intensity (prior to the modulus correction) calculated from the current estimate of the object function.

During the iteration process the most up-to-date guess of the object function provides a running estimate for that object function. When the iteration process is completed as determined by the occurrence of a predetermined event, the running estimate of the object function provides image data over the volume of locations which were illuminated by the incident radiation. This image data includes amplitude and phase information which can subsequently be used to generate a high resolution image of the selected region of the target object.

Embodiments of the present invention thus provide a new method of phase retrieval which is applicable to many situations in microscopy with particular emphasis on its applicability to scanning transmission electron microscopes. The method required as input intensity information only measurements from a small number (one or more) of different probe or aperture positions and this therefore removes the need for post-specimen lenses thus avoiding the problems associated with aberrations of such lenses. The algorithm employed converges rapidly to retrieve the phase of the object transmission function. This enables high resolution images illustrating the structure of target objects to be generated in real time. The algorithm is also effective in noisy situations and works for a very wide variety of different objects and probe functions. Embodiments of the present invention also enable probe functions to be calculated when target objects having a predetermined structure are used.

Figure 9:
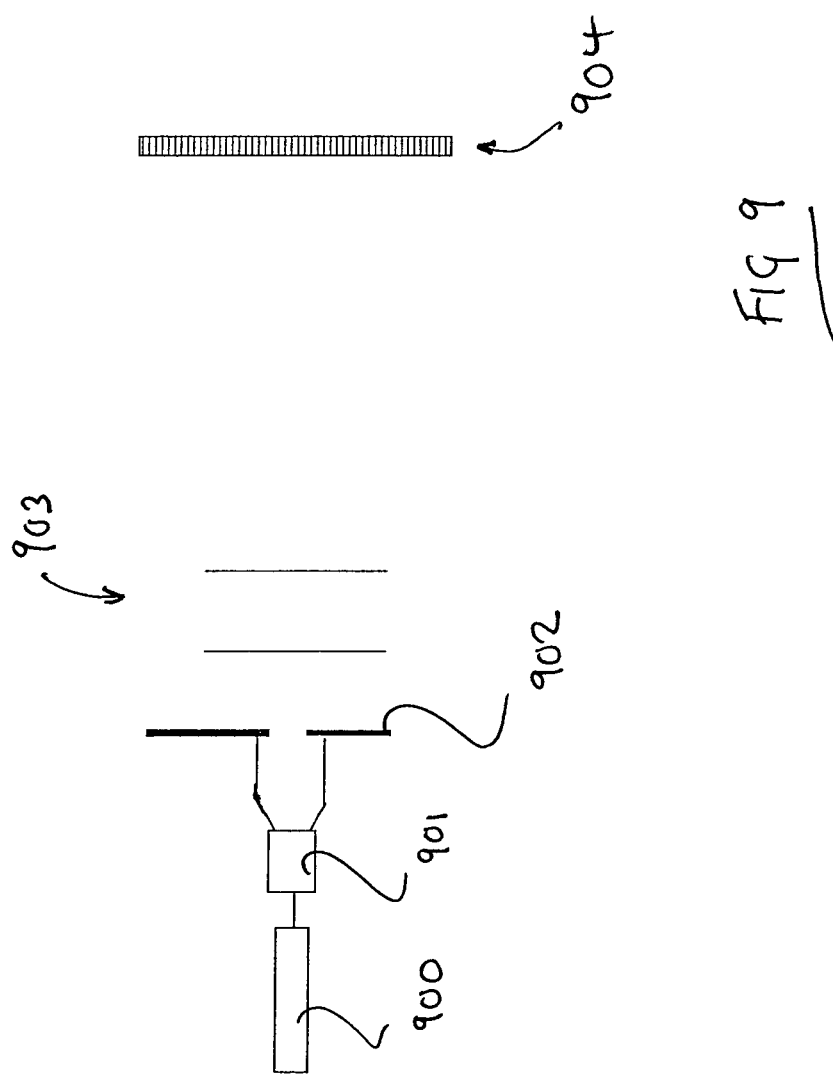
FIG. 9 illustrates a radiation source, aperture, target and detector arrangement.
Figure 10:
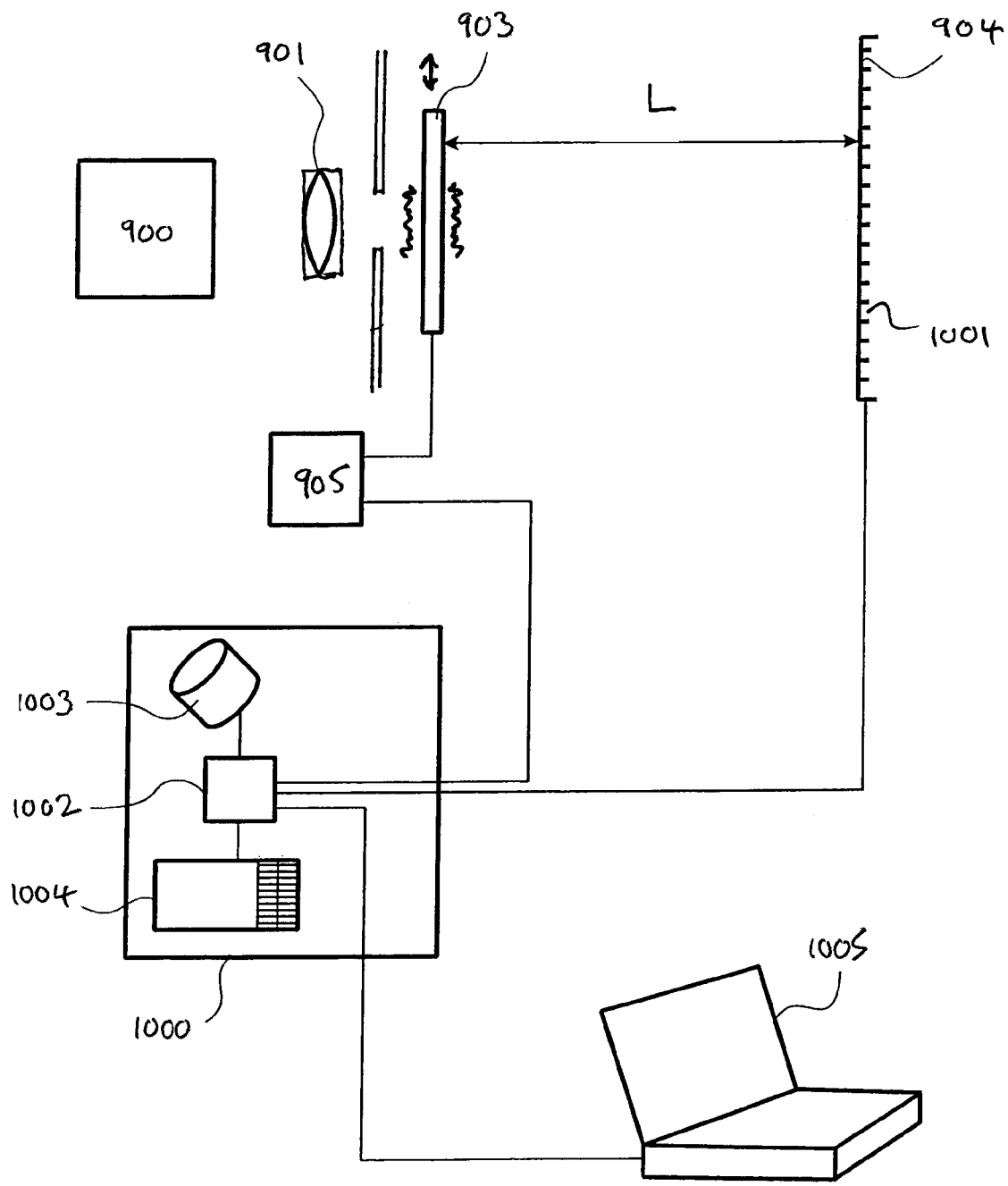
FIG. 10 illustrates a system for 3D examination.

FIGS. 9 and 10 illustrate apparatus for providing image data which may be used to construct a high-resolution image of a region of a target object according to the above-described embodiment illustrated in FIG. 5. A source of radiation 900, such as a laser, provides illumination onto a beam splitter 901 which expands the radiation. An aperture 902 can be moved to enable illumination to fall onto a selected region of a target 903.

The incident radiation has an incident wave function and an exit wave function. This exit wave function is propagated across distance L where a diffraction pattern is formed on an array of detectors 904. The distance L is advantageously sufficiently long so that the propagated exit wave function forms a Fourier diffraction pattern in the far-field. The detector array provides at least one detector which can detect the intensity of radiation scattered by the target object 903. A locating device 905 is provided which may for example be a micro actuator and this can locate the target object at one or more locations as desired with respect to the aperture. In this way radiation from source 900 may be made incident on different locations of the upstream surface of the target 903.

A control unit 1000 provides control signals to the micro actuator and also receives intensity measurement results from each of the pixel detectors 1001 in the detector array 904. The control unit 1000 includes a microprocessor 1002 and a data store 1003 together with a user interface 1004 which may include a user display and a user input key pad. The control unit may be connected to a further processing device such as a laptop 1005 or PC for remote control. Alternatively it will be understood that the control unit 1000 can be provided by a laptop or PC. The control unit can automatically control the production of image data in real time. Alternatively a user can use the user interface or laptop to select areas of the target object for imaging or provide further user input.

In use the source of radiation 900 illuminates the beam splitter 901 with radiation. The target object 903 is selectively located by the actuator 905 under control of the control unit 1000. The radiation forms a diffraction pattern detected at respective locations by each of the detectors in the detector array 904. Results from these detectors is input to the control unit and may be stored in the data store 1003 or laptop etc. If only one position is being used to derive image data the microprocessor uses this detected information together with program instructions including information about the process above-noted to derive the image data. However if one or more further positions are required prior to finalising the image data the control unit next issues signals to the actuator 905 which locates the specimen at another selected location. The actuator 905 may place the specimen at one of many different positions. After relocation a further diffraction pattern formed on the detector array is measured and the results stored in the control unit. As an example the array 904 may be a CCD array of 1200×1200 pixels. If no further intensity measurements are required image data may at this stage be generated by the control unit in accordance with the two newly stored sets of results using the algorithm above-noted. The raw image data may be displayed or a high-resolution image generated from the image data may be displayed on the user interface or remote display on a PC or other such device.

FIG. 11 illustrates results provided by embodiments of the present invention using the arrangements shown in FIGS. 9 and 10. For a 3D target object two projector slides were placed side by side each carrying pre-determined text upon a surface. Data was collected and processed as above described for two values of z, corresponding to the real positions, in the co-ordinate z, of the two slides. Two images both in modulus and phase giving a total of four images were obtained. FIG. 11*a* illustrates the modulus of a first reconstructed image, whilst FIG. 11*b* illustrates the phase of that same reconstructed image. FIG. 11*c* illustrates the modulus information of a second reconstructed image with FIG. 11*d* illustrating the phase of that second reconstructed image. The first pair of images have been calculated with a value of z corresponding to the position of the first project slide, while the second pair have been calculated with a value of z corresponding to the position of the second projector slide. In the first pair of images of FIGS. 11*a* and 11*b* the words "camera" (contained in the first projector slide) are in focus but the letters which are upside down (which are in the plane of the second slide) are out of focus. In the second pair of images the words "camera" are out of focus but the letters which are upside down (which are now in the plane of the second slide as chosen by the value of z used in the reconstruction) are sharply in focus.

The results illustrates performance with two layers in the z direction but can of course be extended according to further embodiment of the present invention to provide a continuous array in the z-direction picking out different layers of the objection. Embodiments of the present invention thus provide an iterative method for deriving image data of a target object. The iterative method is applicable in an intelligent way so as to be able to cope with generalised illumination systems. In these the transmittance function of an aperture is weakly defined or a beam of radiation may be weakly focused. In alternative embodiments rather than deriving information of an object, if the object is well known, information regarding the radiation or aperture itself may be derived.

It will be appreciated that in the prior art, there has been described an algorithm which can be used to investigate two-dimensional (2D) objects using diffracted data collected from a number of probe positions on the assumption that a 2D estimate of the probe can be made at the plane of the 2D object. Embodiments of the present invention can be seen as a novel and inventive progression of this algorithm, wherein the probe is estimated over a number of different planes at different depths throughout the thickness of a three-dimensional object. Those familiar with the art will realise that the extension of such a prior art technique to investigation of three-dimensional objects was previously thought to be impossible to achieve in practice for one or several of the following reasons.

Firstly, it is well-known that iterative phase retrieval methods have difficulty in determining the plane of the object. This is because small displacements of the scattered wave towards or away from the detector plane do not appreciably affect the intensity detected. The success of the above-mentioned prior art technique with 2D objects has therefore been seen to rely on the coincident positions of the two-dimensional object and the particular estimate of the 2D illumination function used in the reconstruction. It was previously to supposed that if any part of an object was not coincident with the plane of the estimated probe, then such an algorithm would be bound to fail, because the data collected would be inconsistent with the assumptions made about the interaction of the probe with the object.

Secondly, for a 3D object, waves scattered from different layers of the object will interfere in the diffraction plane in a way that would render the two-dimensional approximation invalid. This is because, for a given finite angle of scatter, extra phase changes are introduced to waves emanating from different depths of the object. This would suggest that such interference would destroy the opportunity to apply the existing prior art 2D algorithm because it makes no account of such interference effects.

Thirdly, it is known that in 3D objects the illumination function, at planes substantially distant from the entrance surface of the radiation, is altered relative to the free-space illumination function, because of the scattering (or even multiple scattering) from the object itself.

Fourthly, because in the prior art methods only 2D data has been collected. It has until now been felt that this would not encode any 3D information at all. Embodiments of the present invention make use of the unexpected result that despite the previous beliefs that certain techniques would not be applicable to 3D applications certain aspects of prior known techniques can be modified as per the present inventions teaching and quite unexpectedly applied to provide a tool for providing data which can be used to estimate/investigate structure in 3D specimens.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention claimed is:

1. A method of providing image data for constructing an image of a region of a three dimensional (3D) target object, comprising:
    providing incident radiation, from a radiation source, at a target object;
    via at least one detector, detecting the intensity of radiation scattered by said target object with the incident radiation at a first position with respect to the target object;
    re-positioning the incident radiation relative to the target object;
    subsequently detecting the intensity of radiation scattered by said target object with the incident radiation at a second position with respect to the target object;
    selecting a plurality of depths within said target object corresponding to, for each depth, a respective region of the target object which is to be examined;
    determining a probe function at each of the plurality of depths in the target object, wherein each probe function indicates an estimate of at least one characteristic of the incident radiation at the respective depth in the target object; and
    providing image data, as a plurality of sets of data, each data set corresponding to a respective depth in the target object.

2. The method as claimed in claim 1 wherein said providing image data further comprises:
    providing said image data responsive to at least the detected intensity at said first and second positions using a softly varying transmittance function, or illumination function, movable with respect to said target object.

3. The method as claimed in claim 1, further comprising:
    providing images of the target object at the determined depths by sequentially constructing images each corresponding to a respective depth using a respective set of data.

4. The method as claimed in claim 1 wherein said providing said image data comprises:
    estimating an object function indicating at least one characteristic of said region of the target object responsive to detected intensities detected with the incident radiation variously positioned with respect to the target object; an iteratively re-estimating said object function; whereby an accuracy of a running estimate of the object function provided by re-estimating the object function is improved with each iteration.

5. The method as claimed in claim 4 further comprising:
    multiplying the estimated object function by the probe function;
    providing a scattered wave estimate function responsive to a result of said multiplication;
    propagating the scattered wave estimate function to provide an estimate of an expected scattering pattern; and
    correcting at least one characteristic of said expected scattering pattern according to a detected intensity.

6. The method as claimed in claim 5 further comprising:
    inverse propagating the corrected expected scattering pattern to provide an updated scattered wave estimate function; and
    updating the running estimate of the object function responsive to said updated scattered wave estimate function according to the function:

$$O_{n+1}(r) = O_n(r) + U(r)(\psi_{c,n}(r) - \psi_{g,n}(r))$$

where r is a 3D vector represented by Cartesian coordinates x, y, z, $O_{n+1}(r)$ is a running estimate of the object function, $O_n(r)$ is a preceding estimate of the object function or is unity or some other predetermined value when there is no preceding estimate, U(r) represents an update function, $\psi_{c,n}(r)$ is a corrected guess at a scattered wave estimate function and $\psi_{g,n}(r)$ is the current guessed scattered wave estimate function for an iteration.

7. The method as claimed in claim 6 wherein said update function U(r) is:

$$U(r) = \frac{\beta |P(r-R)|^l P^*(r-R)}{|P_{max}(r-R)|^l (|P(r-R)|^2 + \delta)}$$

where R is a probe position moved from the first to second positions, β is a feedback constant, P(r–R) is a probe function at the position R, P*(r–R) the complex conjugate of the probe function P(r–R), $P_{max}$(r–R) is the maximum value of the amplitude of P(r), δ is a selectable parameter and δ is a selectable parameter.

8. The method as claimed in claim 5 wherein said propagating comprises a Fourier transformation when the detected intensity is detected at the far field.

9. The method as claimed in claim 5 wherein said propagating is a Fresnel propagation when the at least one detector is at a distance from said target object where Fresnel diffraction dominates.

10. The method as claimed in claim 1, further comprising:
    selecting said second position so that an area determined in said first position overlaps with a further area determined in said second position.

11. The method as claimed in claim 10 wherein said further area overlaps at least 20% of said an area.

12. The method as claimed in claim 10 wherein said further area overlaps more than 50% of said an area.

13. The method as claimed in claim 5 wherein propagation is calculated according to:

$$M_g(u,v,z) = T_{x,y}^{+1}[\psi_g(x,y,z)]$$

wherein $\psi_g(x,y,z)$ is the scattered wave estimate, where a transform $T_{x,y}^{+1}$ is only taken with respect to the x and y coordinates, whereby for each depth a plane 1 slice over z=constant in $\psi_g(r)$ is Fourier transformed over its x- and y-coordinates and placed into a respective plane 2 slice in $M_g(u,v,z)$ at z=constant.

14. The method as claimed in claim 13 further comprising:
correcting $M_g(u,v,z)$ over the coordinates u and v, to derive a corrected estimate of $M_c(u,v,z)$ according to intensity measured at the detector, for a particular probe position R, via the relationship $$M_c(u, v, z) = \sqrt{I(u, v, R)}\, e^{i\Theta(u,v,z)},$$

where $M_c(u,v,z)$ is the corrected estimate of $M_g(u,v,z)$ where $$\sqrt{I(u, v, R)}$$

is the square root, modulus, of the intensity measured over the detector plane coordinates u and v for the probe position R, and where $e^{i\Theta(u,v,z)}$ is the phase component of $M_g(u,v,z)$, derived from breaking $M_g(u,v,z)$ into its modulus and phase components as it being understood that after this process the modulus of $M_c(u,v,z)$ will thus be constant over all z for each detector coordinate u, v but that the phase $e^{i\Theta(u,v,z)}$ will in general be different for different values of z.

15. The method as claimed in claim 6 wherein said inverse propagation is calculated according to:

$$\psi_c(x,y,z) = T_{u,v}^{-1}[M_c(u,v,z)],$$

$\psi_{c,n}(x,y,z)$ being a corrected estimate of our wave function in real space for an iteration of the calculation, the back transform being undertaken only over the u and v coordinates.

16. A method as claimed in claim 1, further comprising:
estimating the scattered phase and amplitude of waves caused by the object throughout its volume for the $n^{th}$ iteration of the processing algorithm, given by $$\psi_g(r,R) = P(r-R) \cdot O(r) = \psi_g(x,y,z)$$

where $\psi_g(r,R)$ is the scattered wave estimate, where r is a vector, the estimate being applicable for a particular position R of the illumination function $P(r-R)$, and a corresponding particular current estimate of the object function $O(r)$.

17. The method as claimed in claim 16 wherein the first estimate of $O_n(r)$, with n=1, consists of unity amplitude and zero phase over the whole of the volume of r occupied by the object.

18. A method as claimed in claim 7, further comprising:
calculating a 3D illumination function $P(x,y,z)$ via Fourier components of incident plane waves generated, for example, by a lens, such that $$P(x,y,z) = T_{u,v}^{-1}(A(u,v) \cdot e^{i\phi(u,v,z)}),$$

$A(u,v)$ determining a modulus and phase of an angular spectrum of plane waves incident upon the target objects, as a function of the coordinates u and v, and where $$\phi(u, v, z) = \frac{2\pi z}{\lambda}\left(1 - \cos\left(\sin^{-1}\left(\lambda(u^2 + v^2)^{\frac{1}{2}}\right)\right)\right).$$

19. A method as claimed in claim 18 further comprising:
calculating $P(x,y,z)$ from values of phase and modulus at any one predetermined plane, positioned at z=0, $P(x,y,0)$, being such that $$P(x,y,z) = T_{u,v}^{-1}((T_{x,y}^{+1}P(x,y,0)) \cdot e^{i\phi(u,v,z)}).$$

20. The method as claimed in claim 1 further comprising: terminating the iteration process when a predetermined event occurs.

21. The method as claimed in claim 20 wherein said predetermined event comprises the number of iterations satisfying a predetermined condition.

22. The method as claimed in claim 20 wherein said predetermined event comprises a sum squared error satisfying a predetermined condition.

23. The method as claimed in claim 1, further comprising:
positioning the incident radiation with respect to the target object by selecting a location where the incident radiation falls on the target object.

24. The method as claimed in claim 23, further comprising:
selecting the location where the incident radiation falls on the target object by forming an illumination profile with a lens or other optical component.

25. The method as claimed in claim 1 wherein said incident radiation comprises a substantially localized wave field.

26. The method as claimed in claim 1 wherein said image data has a substantially wavelength-limited resolution.

27. The method as claimed in claim 1 wherein said at least one detector comprises two or more detectors.

28. The method as claimed in claim 1 further comprising:
providing said image data for the region of said target object in real time.

29. The method as claimed in claim 1 further comprising:
generating the image of said region on a user display based upon said image data.

30. The method as claimed in claim 1 further comprising:
providing said incident radiation at said target object via a weak lens or a caustic from a reflective surface.

31. The method as claimed in claim 1 further comprising:
locating each said at least one detector in the far field with respect to said target object.

32. The method as claimed in claim 1 further comprising:
locating each said at least one detector at a distance from said target object where Fresnel diffraction dominates.

33. The method as claimed in claim 1 wherein said radiation is scattered via Fourier diffraction and/or Fresnel diffraction.

34. The method as claimed in claim 4 wherein said at least one characteristic comprises amplitude and/or phase.

35. The method as claimed in claim 1 wherein said probe function comprises a time independent 3D illumination function.

36. The method as claimed in claim 4 further comprising:
providing a pre-target aperture between the radiation source and said target object; and
locating the aperture and/or source at different locations to thereby provide incident radiation at said first and second positions with respect to said target object.

37. The method as claimed in claim 4 further comprising:
providing a lens between the radiation source and said target object; and
locating the lens and/or source at different locations to thereby provide incident radiation at said first and second positions with respect to said target object.

38. The method as claimed in claim 36 further comprising:
providing a distance between a lens or aperture and said target object, said distance being sufficient to permit a wave function associated with radiation at an exit location of said lens or aperture to evolve in shape prior to incidence at said target object.

39. The method as claimed in claim 36 further comprising:
detecting the intensity of radiation scattered by said target object with the post target object aperture or the incident radiation at one or more further locations with respect to the target object; and providing said image data via an iterative process using the detected intensity of radiation scattered at least one of the further locations.

40. A non-transitory computer program comprising program instructions for causing a computer to perform the method as claimed in claim 1.

41. A non-transitory computer program product having thereon computer program code means, when said program is loaded, to make the computer execute procedure to display an image of a region of a target object on a user display, image data for generating said image being determined by the computer in accordance with a method as claimed in claim 1.

42. Apparatus for providing image data for generating an image of at least one region of a target object, comprising:
- a radiation source for providing incident radiation at a 3D target object;
- at least one detector device for detecting an intensity of radiation scattered by said target object;
- a locating device that selectively locates the target object at two or more predetermined locations with respect to the incident radiation; and
- a processor that provides the image data responsive to a detected intensity of the scattered radiation at two or more locations,
- wherein the processor is configured to determine a probe function at each of a plurality of depths in the 3D target object, wherein each probe function indicates an estimate of at least one characteristic of the incident radiation at the respective depth in the target object; and
- wherein the processor is configured to provide image data as a plurality of sets of data, each data set indicating structure of a region at the respective depth within said 3D target object.

43. The apparatus as claimed in claim 42 wherein the incident radiation provides a softly varying illumination function.

44. The apparatus as claimed in claim 42 wherein said processor further comprises:
- a microprocessor;
- a data store that holds data and instructions for said microprocessor; and
- a controller that provides instructions to move at least one of said incident radiation or target object.

45. The method of claim 1, comprising:
- constructing an image of one or more regions of the target object via an iterative process using said probe function corresponding to each region.

* * * * *